United States Patent [19]

Mueller et al.

[11] Patent Number: 4,911,793
[45] Date of Patent: Mar. 27, 1990

[54] DISTILLATIVE ISOLATION OF N-ETHYLPIPERAZINE IN THE PRESENCE OF WATER

[75] Inventors: Herbert Mueller, Frankenthal; Dieter Franz, Ludwigshafen, both of Fed. Rep. of Germany

[73] Assignee: BASF Aktiengesellschaft, Ludwigshafen, Fed. Rep. of Germany

[21] Appl. No.: 227,709

[22] Filed: Aug. 3, 1988

[30] Foreign Application Priority Data

Aug. 5, 1987 [DE] Fed. Rep. of Germany ....... 3725925

[51] Int. Cl.$^4$ ...................... B01D 3/14; C07D 295/02
[52] U.S. Cl. ......................................... 203/92; 203/71; 203/73; 203/96; 203/DIG. 11; 544/404
[58] Field of Search ...................... 203/96, 95, 92, 97, 203/71, 73, DIG. 11; 544/404

[56] References Cited

U.S. PATENT DOCUMENTS

| 3,126,383 | 3/1964 | Cooper | 544/404 |
| 3,128,275 | 4/1964 | Lichenwalter et al. | 544/404 |
| 3,154,552 | 10/1964 | Weipert et al. | 544/404 |
| 3,159,633 | 12/1964 | Langdon et al. | 544/404 |
| 4,736,030 | 4/1988 | Mueller et al. | 544/404 |

FOREIGN PATENT DOCUMENTS 181536 5/1986 European Pat. Off. .

*Primary Examiner*—Wilbur Bascomb
*Attorney, Agent, or Firm*—John H. Shurtleff

[57] ABSTRACT

N-Ethylpiperazine is isolated by distillation from a mixture consisting per 100 kg of
a=from 30 to 90 kg of N-ethylpiperazine
b=from 7 to 40 kg of N,N'-diethylpiperazine
c=from 3 to 20 kg of piperazine
d=from 0 to 30 kg of ethanol
e=from 0 to 40 kg of water and
f=from 0 to 5 kg of concomitants, by performing the distillation in the presence of $x=y+e=$ from $3b$ to $12b$ of water, y being the quantity of water which has to be added, if necessary, to meet this condition, and successively separating from this mixture the fractions 1. water, ethanol, N,N'-diethylpiperazine and other highly volatile concomitants,
2. water, if present in excess,
3. piperzine and
4. pure N-ethylpiperazine as overhead products.

6 Claims, No Drawings

DISTILLATIVE ISOLATION OF N-ETHYLPIPERAZINE IN THE PRESENCE OF WATER

The present invention relates to a process for the distillative isolation of N-ethylpiperazine from mixtures thereof with piperazine, N,N'-diethylpiperazine, water and minor amounts of ethanol and other constituents.

N-Ethylpiperazine is an important intermediate for organic syntheses, which in industry is known to be prepared from ethanol and piperazine by various methods. The products are generally mixtures which, besides the N-ethylpiperazine, contain the less desirable N,N-diethyl-piperazine, unconverted piperazine, excess ethanol, water of reaction, and small amounts of some by-products.

As is further commonly known and expressly revealed in EP-A No. 181,536, the distillative working up of these mixtures presents appreciable problems due in the main to the presence of piperazine and water.

According to said EP-A, these problems are bypassed by performing the reaction under certain conditions in the presence of relatively large amounts of water, thereby making it possible to obtain almost complete conversion of the piperazine. The subsequent distillative working up is then significantly simpler since several piperazine azeotropes are absent.

Yet not even this process is fully satisfactory, since complete conversion of piperazine causes a reduction in the selectivity with respect to N-ethylpiperazine and since, in consequence, the inevitable formation of appreciable amounts of the less desirable N,N'-diethylpiperazine must be accepted.

It is an object of the present invention to provide a remedy to both these disadvantages, namely the working up problems on the one hand and the inadequate selectivity with respect to N-ethylpiperazine on the other.

We have found that this object is achieved with a process for the distillative isolation of N-ethylpiperazine from a mixture consisting per 100 kg of
  $a$ = from 30 to 90 kg of N-ethylpiperazine
  $b$ = from 7 to 40 kg of N,N'-diethylpiperazine
  $c$ = from 3 to 20 kg of piperazine
  $d$ = from 0 to 30 kg of ethanol
  $e$ = from 0 to 40 kg of water and
  $f$ = from 0 to 5 kg of other constituents,
which comprises performing the distillation in the presence of. $x = y + e =$ from $3b$ to $12b$ of water, y being the quantity of water which has to be added, if necessary, to meet this condition, and successively separating from this mixture the fractions
  1. water, ethanol, N,N'-diethylpiperazine and highly volatile constituents,
  2. water, if present in excess,
  3. piperazine and
  4. pure N-ethylpiperazine
as overhead products.

This process rests on the surprising observation that N,N'-diethylpiperazine from a mixture of the specified composition combines with water to form an azeotropelike fraction which boils below 100° C. and in this way is easily separated off, although it has a higher boiling point (172° C.) than piperazine (147° C.) and N-ethylpiperazine (156° C.).

The starting mixture is obtained in the various processes known for the ethylation of piperazine with ethanol. Usually this reaction is carried out in the presence of a hydrogenation catalyst and water, frequently also in the presence of water and a mineral base such as sodium carbonate or calcium hydroxide, the ethanol being advantageously used in excess relative to the piperazine.

After the solid hydrogenation catalyst has been separated off, first sufficient of the excess ethanol is distilled off with a small amount of water until an ethanol concentration d is reached. The mixture thus obtained corresponds to the starting mixture of the present process.

Depending on the nature of the preceding ethylation, the starting mixture contains either virtually no water, only the water of reaction formed in the course of the ethylation or, in accordance with EP-A-181,536, water additionally introduced into the ethylation reaction for the purpose of improving the selectivity.

Generally, the ethylation as described in EP-A No. 181,536 shall be preferred, except for the difference that not all the piperazine is converted but only a part, leaving the amount c in the starting mixture according to the invention.

The total amount x of water to be used in the distillation, which is made up of any additional portion y and the amount e already present, depends by definition on the amount b of N,N'-diethylpiperazine, $x = 3b$ being the minimum amount required for separating off the N,N'-diethylpiperazine. In general, however, it is advisable to use somewhat more water, say from $4b$ to $10b$, since the fraction forming the water and the N,N'-diethylpiperazine does not correspond to any azeotrope of constant composition but merely shows azeotropelike behavior. Depending on the residual ethanol content of d and on the measure and amount of the other constituents, the water requirement x varies somewhat, so that a moderate excess is far less disadvantageous than an insufficient amount. Only quantities of water greater than $x = 12b$ do not show any advantage.

At the start of the distillation it is possible to add to the starting mixture all of any water y required, but in general it is more advantageous to add the water gradually at its rate of removal by distillation together with N,N'-diethylpiperazine.

In the first distillation step, which starts at about 80° C., the first cut obtained comprises ethanol, water, N,N'-diethylpiperazine and some of the low-boiling constituents from the synthesis, such as N-ethylethylenediamine and N,N'-diethylethylenediamine.

Thereafter, at between about 80° and 99° C., with the boiling point rising continuously, an azeotropelike fraction comprising a gradually increasing water content and N,N'-diethylpiperazine is obtained.

If water is used in excess relative to the amount required for removing the N,N'-diethylpiperazine, then a second distillation step at about 100° C. produces a second fraction which essentially comprises water.

In the third distillation step, piperazine is obtained as an overhead product at 147° C., and the fourth distillation step gives pure N-ethylpiperazine at 156° C. The bottom fraction remaining behind contains some higher-boiling constituents. The piperazine can be returned into the synthesis, and the N,N'-diethylpiperazine can be separated from the water by extraction with hydrocarbons or by means of concentrated sodium hydroxide solution.

The number of theoretical plates required for separating the four fractions is advantageously from 15 to 40, preferably from 20 to 30, and recommended reflux ratios for the four steps are from 2:1 to 20:1 (step 1), from 2:1 to 40:1 (step 2), from 2:1 to 20:1 (step 3) and from 2:1 to 20:1 (step 4).

All the foregoing particulars apply to working under atmospheric pressure (-1 bar), but there is no reason why the distillation should not also be feasible under subatmospheric or superatmospheric pressure, for example within the range from 0.05 to 10 bar, since the boiling behavior of the starting mixture and of the resulting transient mixtures does not change fundamentally within this range. If a pressure other than atmospheric pressure is employed it will only be necessary to carry out routine trials to determine the specific distillation conditions, such as temperatures, number of theoretical plates and reflux ratios, applicable to the particular pressure.

The process according to the invention can also be made continuous by allocating the four distillation steps as usual to four columns, in which case the number of theoretical plates required in the rectifying section if the distillation is to be carried out under atmospheric pressure is from about 10 to 15 for the first step, from about 20 to 25 for the second step, from about 20 to 25 for the third step and from about 5 to 10 for the fourth step. It is sufficient for the stripping section in each of the four columns to be equipped with about 10 theoretical plates.

As regards apparatus, the process according to the invention presents no problems, so that it can be carried out in a conventional manner in columns of any desired type, preferably including, for economic reasons, packed columns.

The distillation process according to the invention is not discernibly dependent on the provenience of the starting mixture, but in general it is advisable to prepare said starting mixture by the process of EP-A No. 181,536, except that the piperazine is used in larger amounts for improved selectivity with respect to the N-ethylpiperazine, in a piperazine/ethanol molar ratio of from about 0.6:1 to 3:1, and/or that the synthesis is not carried on until all or virtually all the piperazine is consumed.

Since the process according to the invention successfully achieves the object of fractionating piperazine-containing reaction mixtures and isolating the N-ethylpiperazine in pure form, it is no longer necessary to seek substantial conversion of the piperazine, thereby making it possible to reduce the proportion of undesirable N,N'-diethylpiperazine to an economic minimum.

EXAMPLE 1,000 g of a mixture comprising
a = 370 g of N-ethylpiperazine
b = 120 g of N,N'-diethylpiperazine
c = 60 g of piperazine
d = 60 g of ethanol
e = 370 g of water and
f = 20 g of a mixture of N,N'-diethylethylenediamine and
N,N,N'-triethylethylenediamine was admixed with $y = 600$ g of water ($x = y + e = 8.1\ b$) and subjected to fractional distillation under atmospheric pressure in a packed column of about 20 theoretical plates.

While a constant reflux ratio of 3:1 was maintained the following fractions were obtained:

1. at from 78® to 100° C. 655 g of a fraction containing <0.1% by weight of N-ethylpiperazine, 18% by weight of N,N'-diethylpiperazine, 9% by weight of ethanol, 70% by weight of water and 3% by weight of constituents,
2. at about 100° C. 325 g of a fraction essentially comprising water,
3. at 147° C. 60 g of piperazine and
4. at 156° C. 340 g of N-ethylpiperazine.

About 30 g of the holdup remaining as residue at the base of the column essentially comprised N-ethylpiperazine.

The distillation yield of N-ethylpiperazine was thus 92%. If the amount remaining in the holdup is taken into account, which arithmetically tends to zero over several successive distillations, this corresponds to a virtually quantitative yield.

The starting mixture had been prepared by reacting 351 g (4.5 mol) of piperazine and 414 g (9 mol) of ethanol at 175° C. under a hydrogen pressure of 60 bar in the presence of 175 g of Raney nickel and 290 g of water and subsequently removing the bulk of the excess ethanol.

We claim:

1. A process for the distillative isolation of N-ethylpiperazine from a mixture consisting per 100 kg of
a = from 30 to 90 kg of N-ethylpiperazine
b = from 7 to 40 kg of N,N'-diethylpiperazine
c = from 3 to 20 kg of piperazine
d = from 0 to 30 kg of ethanol
e = from 0 to 40 kg of water and
f = from 0 to 5 kg of other constituents,
which comprises:
performing the distillation in the presence of $x = y + e = $ from $3b$ to $12b$ of water, y being the quantity of water which has to be added, if necessary, to meet this condition, and in successive steps separating from this mixture the distilled fractions
3. water, ethanol, N,N -diethylpiperazine and other highly volatile constituents,
2. water, if present in excess,
3. piperazine and
4. pure N-ethylpiperazine as overhead products.

2. A process as claimed in claim 1 wherein the amount of water present in performing the distillation is $x = y + e = $ from $4b$ to $10b$.

3. A process as claimed in claim 1 wherein the amount of water present in the mixture to be distilled is selected in excess of the amount of water required for removing the N,N'-diethylpiperazine.

4. A process as claimed in claim 1 carried out at a pressure of from 0.05 to 10 bar.

5. A process as claimed in claim 1 wherein water is added gradually during the distillation at about the rate of its removal together with N,N'-diethylpiperazine in the first step of the fractional separation.

6. A process as claimed in claim 5 wherein the amount of water present in said first step of the fractional separation is maintained, in excess of the amount of water required for removing the N,N'-diethylpiperazine.

* * * * *

UNITED STATES PATENT AND TRADEMARK OFFICE
CERTIFICATE OF CORRECTION

PATENT NO. : 4,911,793

DATED : March 27, 1990

INVENTOR(S) : Herbert Mueller and Dieter Franz

It is certified that error appears in the above-identified patent and that said Letters Patent is hereby corrected as shown below:

IN THE CLAIMS: Column 4,

Claim 1, line 42: Change the numeral "3" to -- 1 --.

Signed and Sealed this

Twenty-eighth Day of May, 1991

Attest:

HARRY F. MANBECK, JR.

*Attesting Officer*     *Commissioner of Patents and Trademarks*